United States Patent
Seul et al.

(10) Patent No.: US 9,623,050 B1
(45) Date of Patent: Apr. 18, 2017

(54) PATIENT-AND CONDITION-SPECIFIC PLATELET TRANSFUSION SUPPORT

(71) Applicant: BioInventors & Entrepreneurs Network, LLC, Warren, NJ (US)

(72) Inventors: Michael Seul, Basking Ridge, NJ (US); Andreas Gocksch, Centerport, NY (US)

(73) Assignee: Bio Inventors & Entrepreneur's Network LLC, Warren, NJ (US)

( * ) Notice: Subject to any disclaimer, the term of this patent is extended or adjusted under 35 U.S.C. 154(b) by 0 days.

(21) Appl. No.: 15/135,480

(22) Filed: Apr. 21, 2016

Related U.S. Application Data

(60) Provisional application No. 62/278,870, filed on Jan. 14, 2016.

(51) Int. Cl.
| | | |
|---|---|---|
| *G01N 33/48* | (2006.01) | |
| *A61K 35/19* | (2015.01) | |
| *G01N 33/58* | (2006.01) | |
| *G01N 33/60* | (2006.01) | |
| *G06Q 10/08* | (2012.01) | |
| *G06Q 50/22* | (2012.01) | |
| *G06F 19/22* | (2011.01) | |
| *G06G 7/58* | (2006.01) | |

(52) U.S. Cl.
CPC .......... *A61K 35/19* (2013.01); *G01N 33/582* (2013.01); *G01N 33/60* (2013.01); *G06F 19/22* (2013.01); *G06Q 10/087* (2013.01); *G06Q 50/22* (2013.01)

(58) Field of Classification Search
CPC .......... G06F 19/18; G06F 19/22; G06F 19/24; G06F 19/322
See application file for complete search history.

(56) References Cited

U.S. PATENT DOCUMENTS

| | | |
|---|---|---|
| 8,005,622 B2 | 8/2011 | Hauck et al. |
| 2013/0317845 A1 | 11/2013 | Seul et al. |
| 2016/0005139 A1 | 1/2016 | Hammond |

FOREIGN PATENT DOCUMENTS

| | | |
|---|---|---|
| WO | WO2014089478 A1 | 6/2014 |

OTHER PUBLICATIONS

TS Strom, "A Numerical Analysis Model for the Interpretation of in Vivo Platelet Consumption Data" PLOS ONE, Jan. 2013, vol. 8, Issue 1, pp. 1-9.

*Primary Examiner* — Eric S Dejong
(74) *Attorney, Agent, or Firm* — Eric P. Mirabel

(57) ABSTRACT

Determining and implementing individualized platelet support regimens (e.g., administering specified platelet numbers; and, schedules for administration or other intervention, in accordance with the requirements assessed for individual patients) by: monitoring platelet clearance kinetics; analyzing the kinetics to determine value(s) proportionally representing both the extent and frequency of vascular injury, and using such value(s) to determine the momentary requirement for maintaining vascular integrity, and constructing a corresponding platelet administration regimen where said regimen preferably provides for the utilization of platelets selected, from a platelet inventory, in accordance with the recipient's molecular "type". Releasing from an inventory of a platelet inventory system the particular typed or profiled platelet amounts required to satisfy the platelet administration regimen of each patient. Establishing a replenishing inventory of antigen-typed or antigen-profiled platelets or other cells, which are perishable and may be replaced after expiration, where the inventory can be virtual or held across several locations.

20 Claims, 7 Drawing Sheets

TABLE-1

| Time (d) | Normal Subj (16) Autologous 250,000/µl | Patients (7) Autologous 62,000/µl | Patients (13) Autologous 37,000/µl | Patients (6) Homologous 19,000/µl |
|---|---|---|---|---|
| 0 | 1 | 1 | 1 | 1 |
| 1 | 0.9 | 0.87 | 0.83 | 0.71 |
| 2 | 0.8 | 0.73 | 0.68 | 0.51 |
| 3 | 0.7 | 0.62 | 0.55 | 0.36 |
| 4 | 0.58 | 0.51 | 0.4 | 0.22 |
| 5 | 0.48 | 0.42 | 0.3 | 0.14 |

FIG. 4

TABLE-2

| | Parameters | Unit | Vol (ml) | λ/μl/day | σ | Total Plt (/μl) | Circulating Plt (/μl) |
|---|---|---|---|---|---|---|---|
| Source | Off | | 200 | 17,200 | 0.1 | 55,385 | 0.65 |
| Vol Transfused | 200 | ml | Day 1 | 17,200 | 0.1 | 55,385 | 0.65 |
| Unit Vol | 50 | ml | Day 2 | 38,185 | 3,818 | 34,366 | 22,338 |
| Plts/Unit | $5 \times 10^{10}$ | | Day 3 | 17,166 | 1,717 | 15,450 | 10,042 |
| Total Plt Transfused | $2 \times 10^{11}$ | | Day 4 | -1,750 | -175 | -1,575 | -1,024 |
| Total Blood Volume | 5000 | ml | | -18,775 | -1,878 | 16,898 | 10,984 |
| Exp Max Count Increm, Total | 40000 | per μl | | | | | |
| Recovery | 0.65 | | | | | | |
| Exp Max Count Increm, (circ) | 26000 | per μl | | | | | |
| Trigger (circ) | 10000 | per μl | | | | | |
| Exp Max (circ) | 36000 | per μl | | | | | |
| Exp Max Total | 55385 | | | | | | |
| *'Circ' denotes "In Circulation" | | | | | | | |

*FIG. 5*

PATIENT-AND CONDITION-SPECIFIC PLATELET TRANSFUSION SUPPORT

BACKGROUND

In healthy individuals, the level of platelets and other blood cells is maintained in a narrow band by an active feedback mechanism that balances the rate of production with that of loss due to peripheral consumption and clearance. Certain disorders such as bone marrow hypoplasia or acute myelogenous leukemia depress the rate of production, while other conditions, such as certain viral infections, or alloimmunization following exposure to foreign antigens, during pregnancy or as a result of blood transfusion, contribute to accelerated clearance.

In addition, chemotherapy, for patients with hematologic malignancies, impairs or completely suppresses the production of platelets from megakaryocytes (HarkerFinch1969), and even with finite residual production, platelet function in such patients may be impaired. Thus, Psaila2012 reports reduced expression levels of membrane glycoproteins including GPIb which binds to von Willebrand factor on (sub-)endothelial cells at sites of vascular injury ("lesions") and thereby mediates platelet adsorption.

Hemorrhages of varying degree of severity remain a principal factor contributing to morbidity and mortality of patients receiving chemotherapy for hematologic malignancies, including bone marrow transplant candidates. While low platelet count per se may not be the cause of bleeding, it may exacerbate the risk of an insufficient response in the event (HoTin-Noe2011, Loria2013). Under current treatment guidelines (Slichter2005), patients receiving chemotherapy are managed in accordance with "one-size-fits-all" algorithms including triggers for prophylactic platelet transfusion. Many clinical studies over the past decade or more have sought to identify an "optimal" value for such a trigger, often by looking for a significant increase in frequency and severity of bleeding episodes at lower platelet count (Estcourt2012). At present, only "bleeds" causing visible symptoms (including petechiae, bruises or external blood loss) are routinely monitored or assessed during treatment, and changes in transfusion trigger, while often based on bleeding episodes, may not be correlated to the trigger levels, or changes thereof seSee, -Rioux-Masse B, Laroche V, Bowman R J et al. The influence of bleeding on trigger changes for platelet transfusion in patients with chemotherapy-induce thrombocytopenia Transfusion. 2013 February; 53(2): 306-14.

However, inflammation, has been has been recently shown to cause of bleeding by impairing vascular integrity (Ho-Tin-Noe2011), and platelets have been shown to be "vital in maintaining vascular integrity (Nachman2008), especially in inflamed tissue (Goerge2008) This is a concern for patients receiving chemotherapy who frequently present with symptoms of inflammation, ranging from fever to sepsis.

Recent work indicates a role of platelets, beyond that of maintaining hemostasis, in modulating inflammatory reactions and immune responses by direct interaction with leukocytes and epithelial cells and by releasing inflammatory mediators (Assinger2014). In fact, transfusions themselves are known to be associated with an increased risk of infection as well as inflammation, where the latter may be caused or exacerbated by chemotherapy (vanderMost2008) and by hemolytic transfusion reactions (Strobel2008). Moreover, it has been observed, in a mouse model, that severe platelet deprivation leads to splenic necrosis, with deleterious effects on innate and adaptive immune responses to certain infectious agents (Loria2013).

Thus, individual requirements for maintaining vascular integrity may change over time, and may differ between patients, in a manner reflecting inflammatory and perhaps other clinical conditions.

Accordingly, a method is needed to determine individual transfusion regimens, especially for severely thrombocytopenic patients, by assessing the individual (and possibly time-varying) need for support in relation to the condition of the patient, by assessing that condition, non-invasively and continually, and determining the requirement for maintaining an adequate level of platelets in circulation to ensure a protective immune response, and satisfying the demand for platelets in maintaining vascular integrity. To ensure adequate quantities of antigen-profiled platelets are available to needy patients, and to reduce cost, the method should avoid excess utilization of platelets (and related services), such as the administration of any particular antigen-profiled platelets. The method may also ensure that patients who may have developed allo-antibodies to platelets are administered sufficient quantities of platelets of the correct type to ensure a protective immune response, and maintain vascular integrity.

SUMMARY

The invention relates to treating patients and managing inventories of cells, particularly platelets. It includes methods to manage the transfusion support of patients in accordance with individual conditions, by providing a method for monitoring and assessing, in real time, the demand for platelets in maintaining vascular integrity and, on the basis of that assessment, determining an individual cell administration regimen for administering platelets or other cells— where the cells or platelets are preferably typed or profiled; and where the regimen avoids or minimizes excess administration of such platelets or other cells.

The methods of the invention comprise: determining and implementing individualized platelet support regimens (e.g., administering specified platelet cell numbers; and, schedules for administration or other intervention) by: monitoring platelet consumption kinetics; analyzing the kinetics to determine value(s) proportionally representing both the extent and frequency of vascular injury, estimating from these values a minimal demand for platelets (per time period, say 1 day) in repairing vascular injury, and using such value(s) to determine the momentary requirement for maintaining vascular integrity, and constructing a corresponding platelet administration regimen.

Preferably, the regimen utilizes typed or profiled platelets in accordance with the molecular attributes of patients, and comprises releasing from the platelet inventory system the particular typed or profiled platelet amounts required to satisfy the platelet administration regimen of each patient. Excess administration of particular typed or profiled platelets is avoided. Tracking of such cells, held in inventory for administration, ensures availability of needed typed cells, when required, and significantly enhances public health. The invention further relates to establishing a replenishing inventory of antigen-typed or antigen-profiled platelets or other cells, which are perishable and may be replaced after expiration, where the inventory can be virtual or held across several locations.

In another embodiment of the invention, an individual's platelet requirement is satisfied by adopting an optimized administration regimen whereby platelets are selected in accordance with the patient's molecular attribute profile and/or antigen status in order to avoid antibody binding and premature platelet removal. If the patient has formed antibodies in response to exposure to foreign antigens during pregnancy or by previous transfusion, or, on the basis of his or her antigen profile, is at risk of making antibodies in response to exposure to foreign antigens expressed on platelets from random donors, then such antibodies, by binding to such transfused platelets, mark the platelets for instant removal, as if they were senescent. To avoid exposure to such foreign antigens, the optimized administration regimen is used to maintain sufficient platelet levels.

BRIEF DESCRIPTION OF THE FIGURES

FIG. 4 shows a Table 1, which is a summary of survival curves of $^{51}$Cr-labeled platelets injected into normal subjects, with a pre-transfusion circulating platelet count of 250,000/µl and three groups of patients with bone marrow hypoplasia of differing severity, indicated by the decreasing pre-transfusion circulating platelet counts (FIG. 1 in Hanson&Slichter1985). For each group, the fraction of $^{51}$C-labeled platelets surviving is shown as a function of time.

FIG. 5 shows a Table, which is a worksheet illustrating the determination of the rate λ (per µl per day) of consumption of platelets in maintaining vascular integrity that, in combination with the loss of platelets due to senescence, at a rate σ, expressed as a fraction of the number of platelets remaining in circulation, ensures a decrease in the circulating platelet count from the expected maximum attained immediately following a transfusion with the specified "Parameters," (as indicated in the column) to the level of 10,000/µl (at which point intervention is triggered) within a preset period, here 2 days. Note that all values less than 0, i.e., negative numbers, are to be ignored.

DETAILED DESCRIPTION

Definitions

Figure 1:
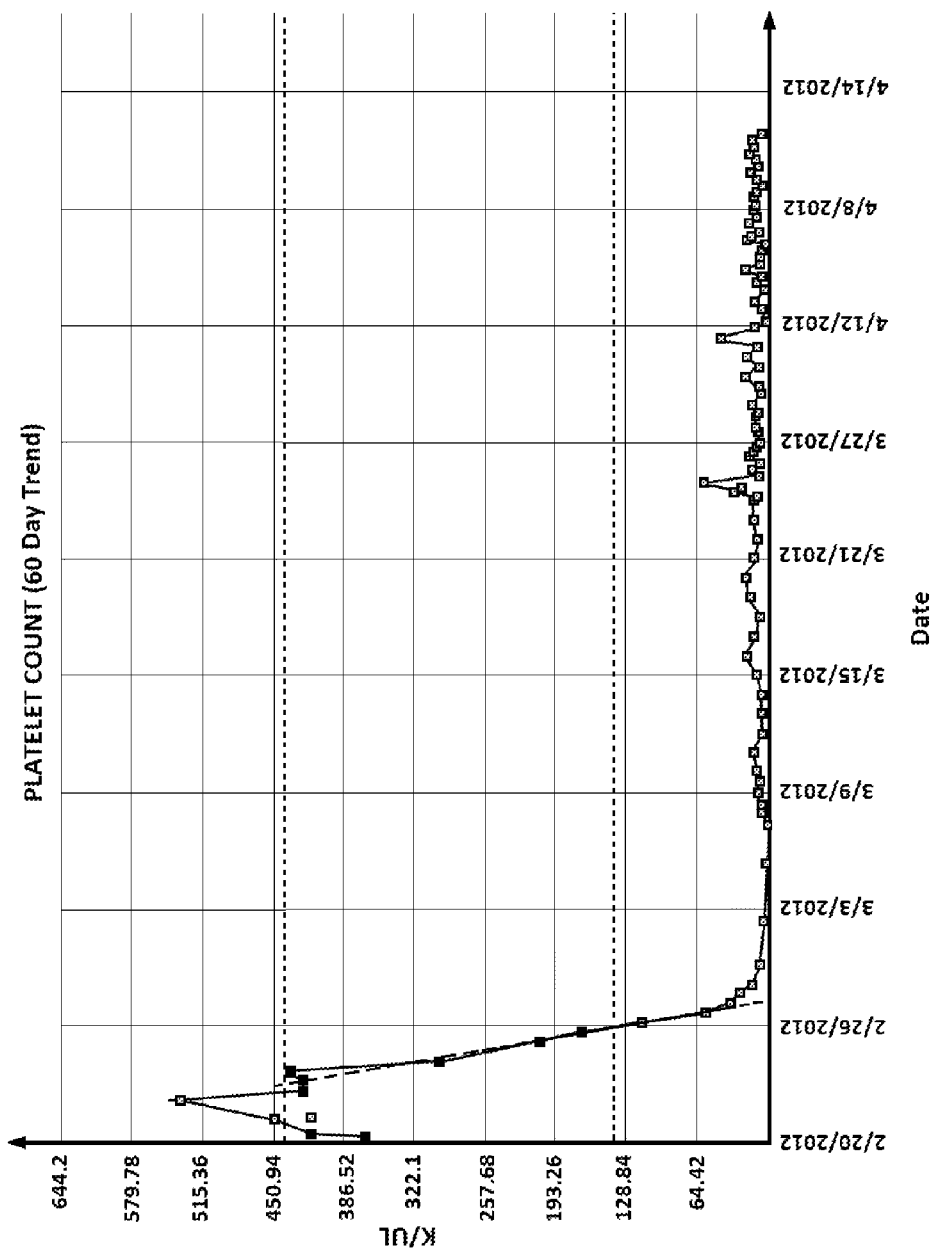
FIG. 1 is a graph recording platelet count by date for a patient receiving transfusions in support of chemotherapy. There is an initial steep linear decay in platelet count, indicated by the dashed line, from levels at the upper end of the normal range (indicated by the two horizontal lines at approximately 130 K/µl and 450 K/µl) to approximately 60 K/µl.

"Platelet requirement" or "platelet transfusion requirement" refers to not substantially less than the amount of platelets required to be transfused to a patient to repair the estimated vascular injury and replenish platelets lost to senescence; where "not substantially less" refers to the amount of platelets required to produce a platelet concentration within a range of 10,000/µl, or preferably 5,000/µl or preferably 1,000/µl of the platelet concentration meeting the platelet requirement. "Instantaneous platelet requirement" refers to a platelet requirement determined to exist for a specific patient at a specific time "Administration regimen" or "support regimen" refers to a schedule of platelet administration comprising amounts and types of platelets or other cells administered in accordance with a determined mode (such as continuous or intermittent) at a specific rate wherein mode or rate may vary with time. "Optimized administration regimen" or "optimized support regimen" refers to an administration or support regimen that is optimized by selecting platelets in accordance with a molecular attribute of the intended recipient The invention includes a novel method for determining an individual platelet transfusion requirement, where, first, one assesses vascular injury by monitoring and analyzing platelet survival curves. For patients receiving chemotherapy, the survival curves may be recorded by taking periodic readings of the circulating platelets following a platelet transfusion. Next, one determines an individual platelet treatment regimen, reflecting the platelet requirement so determined. The regimen includes constructing a prescription of the number of platelets to be administered, and a schedule of administering said number of platelets including the possibility of continuous administration. In one embodiment, the prescription calls for the number of platelets given to be no less than the momentary rate of platelet consumption in the repair of vascular injury. In another embodiment, the prescription calls for the number of platelets to be given to be sufficiently large to ensure that the count stays above a preset threshold for at least a preset time, Δt. In yet another embodiment, the prescription calls for maintaining platelets at or near constant level, by setting the rate of infusion to balance or approximately balance the rate of loss.

By using the method of determining a platelet administration regimen and prescription in relation to a patient's condition, by reducing platelet utilization, platelets of particular types are preserved without risking adverse events for the patient. The inventory of platelets of particular types is tracked, when: they reach expiration, or are removed from inventory for administration, or are replenished. The inventory can be a virtual inventory of antigen-profiled platelets or cells, as described in US Publ'n No. US 2013/0317845 (incorporated by reference). In US Publ'n No. US 2013/0317845 the virtual inventory exists between an exchange and multiple entities which actually hold the inventory, and can involve a conditional sales agreement between the exchange and such entities, where the exchange has rights to specific inventory covered under the agreement.

Non-Invasive Assessment of Vascular Injury by Analysis of Platelet Survival Curves At least two processes contribute to platelet consumption:
1. the steady removal of senescent platelets, in healthy individuals at a daily rate of ~10% of the total number (Harker1969), as determined by an internal molecular clock (Dowling2010). In patients with existing antibodies directed to antigens expressed on the surface of platelets, notably including Human Leukocyte Antigens of class I ("HLA class I") and Human Platelet Antigens ("HPA"), platelet opsonization marks platelets for clearance, thereby significantly reducing the normal platelet lifespan of ~10 d. (Harker1969). Thus, for present purposes, unless explicitly mentioned, we include the clearance of antibody-decorated ("opsonized") platelets under senescence; and
2. the recruitment of platelets to sites of vascular injury as an integral part of the process of maintaining vascular integrity: an estimate of $7,100/\mu l*day$, in Hanson1985, has been widely cited in the literature; more recent work, on mouse models, places the estimate at 10-15% of the normal platelet level, corresponding, in humans to $35,000/ul-47,500/u$ (Loria2013).

Assuming this range of values, loss of platelets to senescence will be the pre-dominant process at normal levels; however, at low platelet levels, when the contribution to senescence (in the absence of antibodies) drops to low values, the fixed consumption in the repair of vascular injury may dominate. Hence, for patients with impaired platelet production, either congenital or acquired, the latter especially as a result of chemotherapy, it will be critical, in order to construct an optimized platelet prescription (quantity of platelets and interval of administration in relation to a momentary platelet requirement) to better understand the vascular repair process. Particularly important in this context is the observation, in recent work on a mouse model, that inflammation causes bleeding in thrombocytopenia, and that platelets are "indispensable to maintaining vascular integrity in inflamed tissue." (Goerge2008).

Platelet Survival Curves

Over a period of 35 years, from the early fifties to the mid-eighties, the fundamentals of thrombokinetics, including the lifetime of platelets in circulation, their sequestration in spleen and liver, and the disorders of platelet production, distribution and consumption, were elucidated by injecting isotopically labeled platelets into normal subjects as well as patients with various disorders, and monitoring the decay of radioactivity over time, thereby generating survival curves (HarkerFinch1969). Labeling is necessary whenever the platelet level remains constant. When platelet production is attenuated or completely suppressed, counts may be determined directly, using a hemocytometer or other method of particle counting. Platelet survival curves simply record the count of labeled or unlabeled platelets remaining in circulation as a function of time after transfusion. Often, counts are normalized in a convenient manner, for example, for labeled platelets: to an initial reference level of radioactivity or fluorescence, or, for unlabeled platelets, by computing a corrected count increment.

Modeling Vascular Injury Repair as a Stochastic Process

The methods herein represent the process underlying the consumption of platelets in the repair of vascular injury as a stochastic process. Vascular injury is modeled in the form of lesions in the vasculature, which arise spontaneously, in accordance with a Poisson process of rate $\lambda$, and exponentially distributed severity or size, with mean $\mu$. This stochastic process generates an average requirement for $\lambda\mu$ platelets over a characteristic time period, say a day. In combination with the clearance of senescent platelets, at an internally preset rate a, the consumption of platelets in the repair of vascular lesions determines the kinetics of the platelet count evolution which may be recorded in the form of platelet survival curves.

Contrary to a widely cited view (Hillyer C D. Blood Banking and Transfusion Medicine: Basic Principles & Practice. Churchill, Livingstone, Elsevier, $2^{nd}$ Ed, 2007. Chapt 33, p 458), originating with Hanson & Slichter (Hanson19985), that the platelet requirement for repairing vascular injury is a fixed requirement, the re-analysis of published survival curves using a stochastic model of vascular injury repair as disclosed herein does not support a fixed requirement (see also EXAMPLE 2, below). Rather, the number of requisite platelets is shown to depend on the patient's condition. Thus, a need arises to assess, in individual patients, the minimal level of platelets required to support the critical function of repairing vascular injury.

The method of the invention comprises the steps illustrated by the following pseudo-code:

```
# Definitions
σ:  rate of removal of senescent platelets, that is: the percentage of platelets that have sur-
vived
    to the end of their natural lifespan of typically 10d; thus, a typical value would be ≤10%
    per day of the total number of platelets.
λ:  the daily rate of occurrence of lesion "events", expressed as a number of platelets per µl
    per day: typical values may be in the range 5,000/µl to 15,000/µl.
µ:  the mean value of lesion size, expressed as the number of platelet consumed in the repair
    of a lesion of that size; thus, λµ represents the mean number of platelets consumed per
day
    in maintaining vascular integrity.
π:  daily rate of production of platelets; in a healthy individual; typical value: 35,000/µl
    (Harker&Finch1969).
N₀: total number of platelets, including those sequestered in spleen; typical value for a
healthy
    individual: 350,000/µl, where typically 1/3 of this number is sequestered in the spleen
    (Aster1966).
Φ₀: percentage of labeled platelets, if any; typical value: 5-10% if autologous, 50% if
    homologous platelets are used for generating survival curves.
T:  maximum run time, in days; typical value: 10.
# define function
C <- function(n,UseExp=TRUE)
{
    # set event size by sampling from a constant (UseExp=FALSE) or
    # from an exponential (UseEXp=TRUE) event ("lesion") size distribution
    # n: integer, specifying mean event size
```

-continued

```
    # UseExp: logical: if set, use exponential, otherwise constant event size distrib
    return(if(UseExp) n*rexp(1) else n/exp(1))
}
# load data (to which model simulation is to be compared)
sCurve <- loadData(patientPlateletSurvivalCurve)
# initialize parameters (NOTE: λ, μ are the only adjustable parameters)
(λ, μ, σ, π) <- initializeParameters( )
(N₀, (Φ₀)) <- initializeParameters( )
T <- initializeParameters( )
# initialize variables using parameters set above
I <- 1                          # indicator variable
t <- 0                          # elapsed time
te <- -log(runif(1))/ λ         # time of next event for Poisson proc
b <- b0 <- (1- Φ₀)* N₀          # b ("blue"): unlabeled plt;
r <- r0 <- Φ₀* N₀               # r ("red"): labeled plt
db <- 0; dr <- 0;               # differentials for b, r
# initialize data structure holding simulation outputs
bPath <- as.vector(b)           # holds number of unlabeled platelets
rPath <- as.vector(r)           # holds number of labeled platelets
dbPath <- as.vector(0)          # holds decrement of unlabeled platelets
drPath <- as.vector(0)          # holds decrement of labeled platelets
tePath <- as.vector(te)         # holds event ("lesion") times
ePath <- as.vector(0)           # holds event ("lesion") sizes
# main loop
while( (te <= T) & (I ==1) ) }
# evolution of r and b platelet counts reflecting senescence and residual production of unla-
beled
plt
b <- b - σ*b0*(te-t) + π *(te-t) # balance of unlabeled plt: senescence and residual prod
r <- r - σ*r0*(te-t)            # balance of labeled plt: senescence
# vascular "lesion" event, at t=te:
evSize <- C(μ,UseExp)           # total plt consumed in event (= repair of vascular
lesion)
db <- evSize*b/(b+r)            # compute number of unlabeled platelets consumed in event
dr dr <- evSize*r/(b+r)         # compute number of labeled platelets consumed in
event
b0 <- b0 - ((b- π *(te-t))/b)*db # adj b0 by fraction of ORIGINAL "b" plt consumed in
event
r0 <- r0 – dr                   # adj r0 by fraction of ORIGINAL "r" plt consumed in event
b <- b - db                     # adj number of "currently" remaining unlabeled
platelets, b
r <- r - dr                     # adj number of "currently" remaining labeled platelets, r
if( (b <= 0)|(r <= 0) ) I <- 0  # check whether unlabeled and labeled plts remains positive
t <- te                         # update elapsed time
te <- t - log(runif(1))/λ       # generate new event time
    # record simulation output(s) ("book keeping")
    bPath <- c(bPath,b)
    rPath <- c(rPath,r)
    dbPath <- c(dbPath,db)
    drPath <- c(drPath,dr)
    tePath <- c(tePath,te)
    ePath <- c(ePath,evSize)
{
```

The main loop may be deployed as part of a standard non-linear regression routine such as the R function "nls2" (see e.g., website entitled "Non-linear regression with brute force" by G. Grothendieck) seeking optimal values for $\lambda$, $\mu$, $\sigma$ and $\pi$ so as to minimize an $r^2$-value computed from fits, notably the survival curve of labeled platelets (in rPath) or unlabeled (in bPath) and data (in sCurve). Typically, $\pi$, and, in some cases (for example for normal subject or patients, with high platelet count), $\sigma$, would be held fixed at their respective initial values, and only $\lambda$ and $\mu$ would be varied. The optimal values for the latter two parameters then directly provide frequency and typical size of randomly occurring vascular lesions, in terms of the number of platelets required for lesion repair. In actual fact, what matters is the total, $\lambda\mu$, of platelets consumed in vascular lesion repair. Thus, when sampling event sizes from a constant distribution (UseExp=FALSE), the stochastic process simplifies to a pure Poisson process and $\mu$ may be set to 1 without restriction of generality.

For platelet curves recorded with labeled platelets, the method of the invention yields curves which may vary in shape from linear to exponential, depending on the rate of production, $\pi$. For platelet survival curves recorded without labeling, the method of the invention yields a linear decay. In either case, $\lambda$ and $\mu$ may be directly extracted from the regression analysis.

Thus, in contrast to the view expressed in the literature, namely "that analysis of platelet survival curves may not provide insight into the mechanism normally responsible for the removal of platelets from circulation" (Hanson1985 and refs therein), the method of the invention, by way of analyzing survival curves, permits the determination of the relevant parameters, $\lambda$, $\mu$ and $\sigma$; in addition, the method permits the detection of alloimmunization, which manifests itself in the form of accelerated senescence. In essence, this embodiment of the invention converts the platelet count evolution captured in the form of a survival curve into an internal indicator for the frequency and size of vascular lesions consuming a fraction of the platelets in circulation.

To the extent that the frequency and size of vascular lesions reflect inflammation, this determination also would represent a non-invasive method of assessing the "internal" inflammatory condition of the patient's vasculature.

In-Vivo Evaluation of Graft Donor Compatibility

A further application of the method of the invention is that of evaluating the recipient immune response to HLA-class I and/or HPA antigens expressed on the platelets of a prospective organ or stem cell donor. Radioactively or fluorescently labeled platelets, collected from the prospective donor, would be prepared by standard methods (Harker1969), injected into the recipient, and monitored to determine a survival curve for the labeled platelets, generating data such as those in Table 1. Differential labeling, e.g., with different fluorescent dyes, and monitoring by standard flow cytometry would permit the analysis of the differential clearance kinetics for the recipient's own platelets compared to that for the prospective donor platelets and thereby permit an assessment of the anticipated adverse immune response to a stem cell or organ graft expressing HLA-class I and/or HPA antigens.

Dosing by Individual Platelet Requirement

An additional aspect of the method of the invention is the administration of platelets in accordance with a dosing regimen reflecting the platelet requirement of individual patients at specific times, as determined from the platelet clearance kinetics, in accordance with the methods disclosed herein.

Transfusion Service Performance Assessment

In one respect, the invention provides a process for assessing the allo-antibody status of a patient population. Given the common current clinical practice of performing an antibody status determination ("screen") and specificity determination only in special circumstances, such as in connection with the evaluation of hematology patients as stem cell transplant candidates, this process is especially useful as a means to assess the expected burden of managing patients expected to have, or to develop, antibodies directed to platelets (and by extension to other cells such as red cells), given that sensitized patients require support with special platelets and/or other cells selected to minimize adverse immune reactions; further, the process permits an assessment of the performance of providing this type of special support, assessed by the degree to which further sensitization (ak alloimmunization) has been avoided.

Figure 2A:
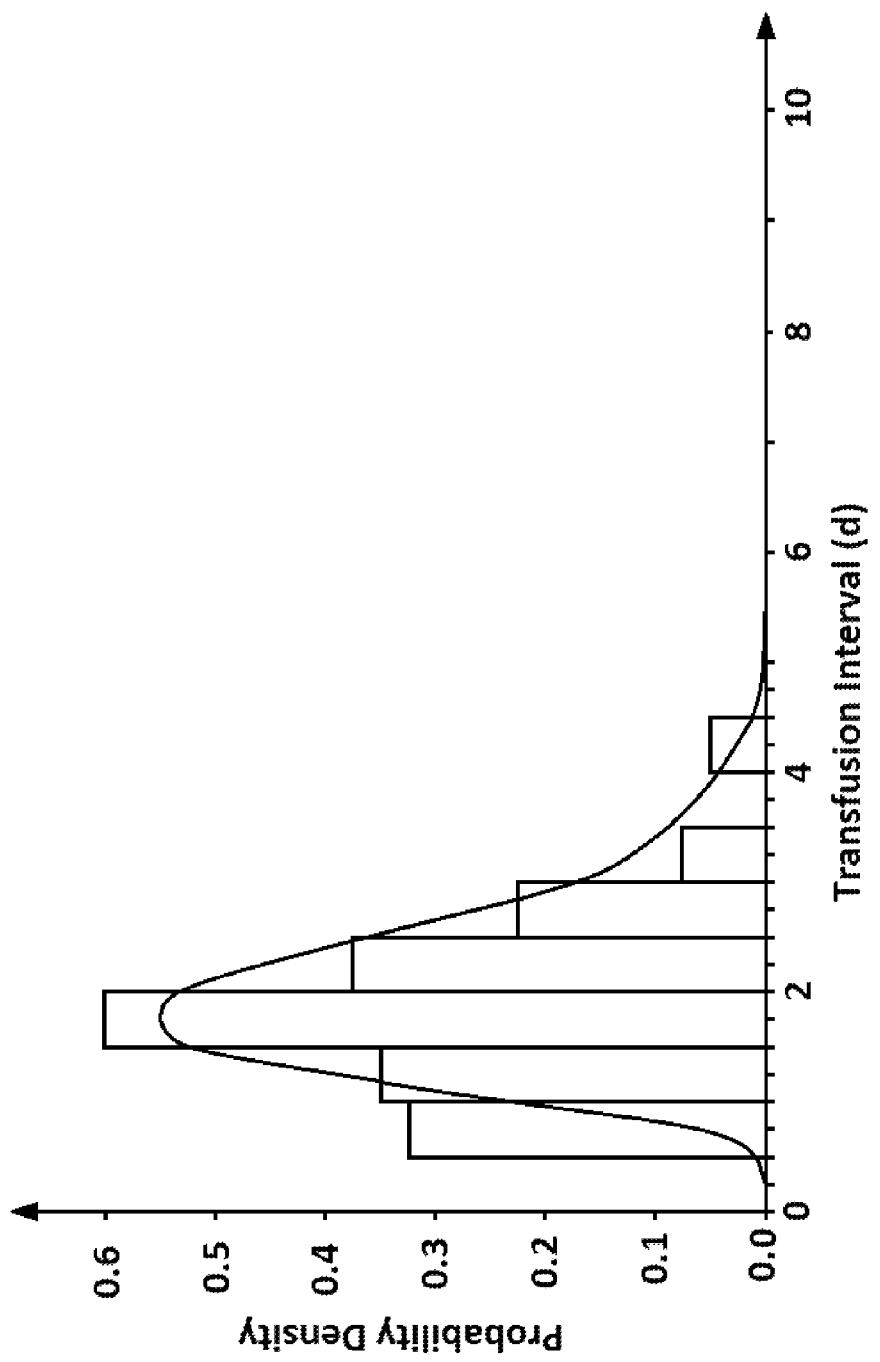
FIG. 2A is a histogram (probability density vs. transfusion interval) of mean values of histograms of transfusion interval sets for a group of ~200 antibody-negative patients receiving platelet transfusions in support of chemotherapy for hematologic malignancies. The solid line represents the gamma distribution with shape and scale parameters determined from the moments of the histogram, with mean=2.1 and variance=0.65.
Figure 2B:
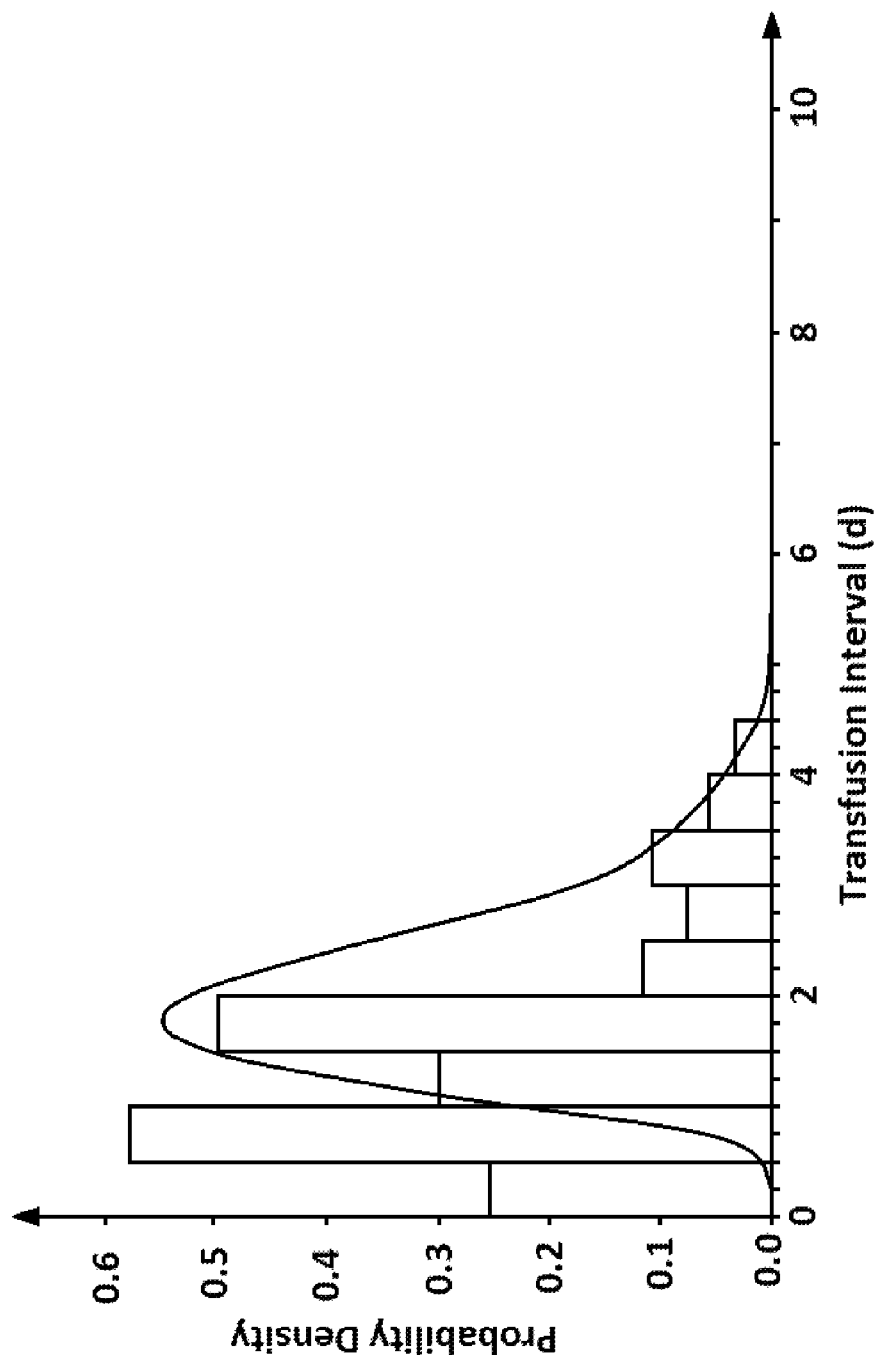
FIG. 2B is a histogram of mean values of histograms of transfusion interval sets for a group of ~200 patients (different from the group of patients in FIG. 2A, and including some antibody-positive patients) receiving platelet transfusions in support of chemotherapy for hematologic malignancies; as in FIG. 2A, the solid line represents the gamma distribution with shape and scale parameters determined from the moments of the histogram, with mean=2.1 and variance=0.65; in contrast to FIG. 2A, the histogram now is bi-modal, displaying an additional ("fast") peak, at <1, attributable to a process of antibody-mediated platelet clearance that operates in parallel with the process of vascular injury repair described by the process of the invention.
Figure 3:
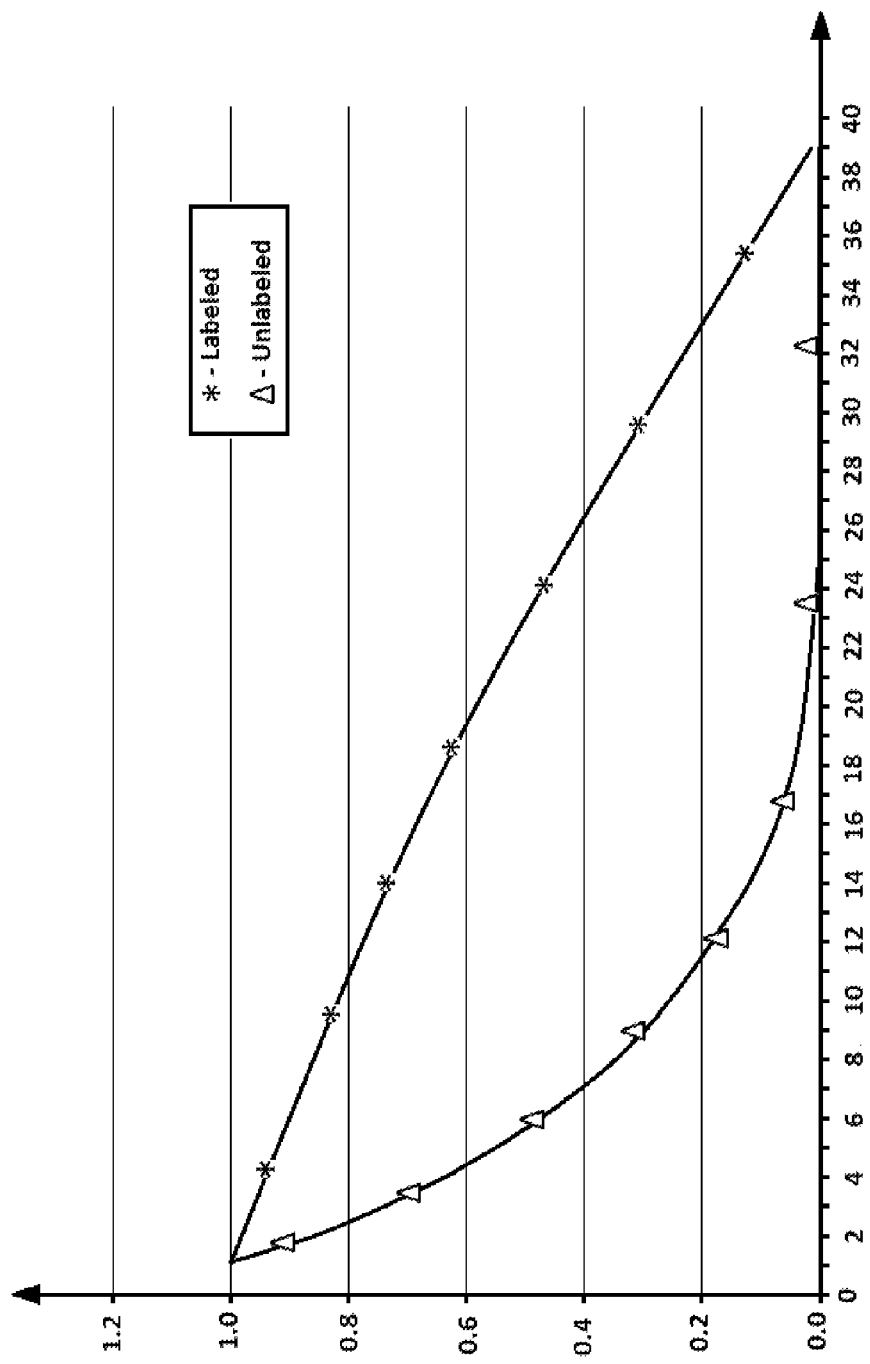
FIG. 3 shows examples of survival curves for labeled and unlabeled platelets, predicted by the stochastic model of vascular injury repair. The x-axis shows time, in days, the y-axis shows the fraction of initial labeled and unlabeled platelets surviving.
Figure 6:
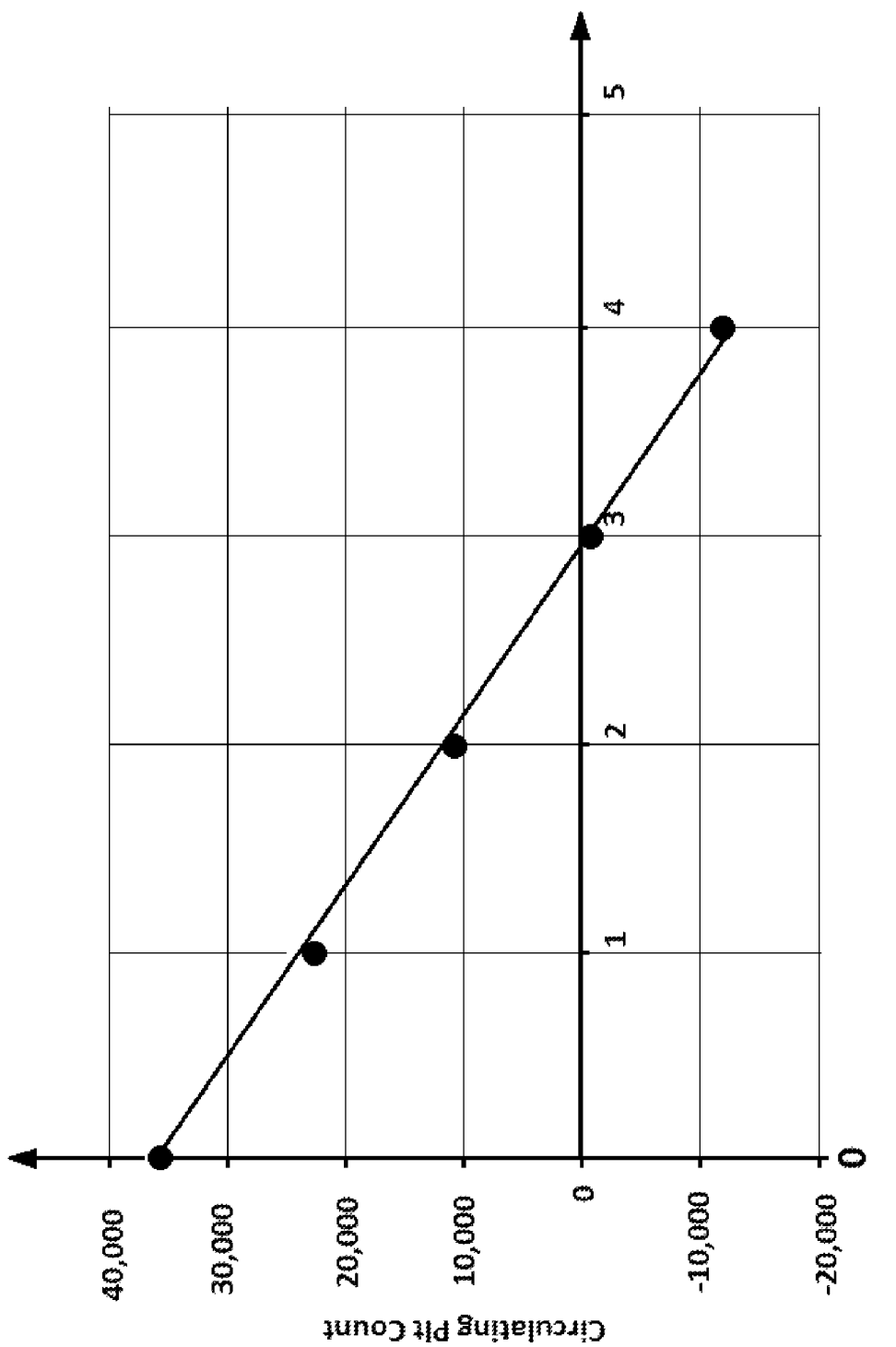
FIG. 6 shows a plot of "Platelet Count Decay," displaying the decrease in platelet count as a function of time. Note that all values less than 0, i.e., negative numbers, are to be ignored.

This assessment proceeds by analysis of platelet transfusion records, and especially of the distribution of transfusion intervals—that is: the time between successive transfusions—in order to estimate the percentage of patients in a selected sample population with antibodies directed to antigens expressed on platelet surfaces. This process comprises the following steps:

- construct histograms of the histogram means for individual transfusion interval series such as those in FIG. 2A and FIG. 2B herein;
- applying the stochastic process of the invention, determine the contribution to platelet clearance attributable to vascular injury repair (see also Example 3). In a preferred embodiment, this step comprises parametrization in terms of a gamma distribution and reference to parameters determined for populations of patients known not to have been sensitized;
- identify any (remaining) contribution to the histogram not attributable vascular injury repair and attribute it to antibody-mediated clearance. Note thatFIG. 2B displays a peak at ~2 d attributable to the vascular injury repair process and a resolved "fast" peak, at <1 d, attributable to the antibody-mediated clearance process;
- estimate the magnitude of relative contributions to the clearance kinetics of the two processes operating in parallel, namely: vascular injury repair and antibody-mediated clearance, by comparing respective peak areas or amplitudes: these provide estimates of the proportion of "fast" transfusion intervals observed in the transfusion record;
- estimate the proportion of antibody-positive and antibody negative patients in the population described by the transfusion records, by bootstrap sampling of the population, with reference of the probability, $S(n)=\text{prob}(N>n)$, that a patient receives in excess of N transfusions.

In another embodiment of the invention, the regimen of administering platelets may be adjusted for patients so as to increase the volume transfused, thereby increasing the platelet count attained immediately following transfusion (see also: Example 3, below), thereby increasing the time to the next transfusion; and reflecting the operation of only the process of vascular injury repair. As the "fast" peak reflecting the operation off antibody-mediated clearance will remain unaffected, such an adjustment in transfused volume will increase the peak resolution in any bimodal histogram such as that in FIG. 2B.

In another respect, the method of the invention permits a real-time determination of the demand for platelets in maintaining vascular integrity (namely by mediating the repair of vascular injury). This demand may vary over time, reflecting, for example, the patient's inflammatory condition (Ho-Tin_noe2011). Thus, in contrast to the recommendation in current clinical guidelines, of relying on a universal minimal preset value of the platelet count to indicate a prophylactic platelet transfusion, the method of the invention permits the platelet support to be based on an individual value that that is close to the actual demand for platelets for the repair of vascular injury. This allows avoidance of over-administration of platelets.

The methods of the invention are illustrated by the following examples.

Example 1

Determine $\lambda\mu$ from platelet count evolution for a patient receiving chemotherapy, with negative anti-HLA screen FIG. 1 is a survival curve for a leukemia patient, generated by recording platelet count at approximately daily intervals following initiation of chemotherapy (hence at least partial suppression of platelet production). A linear fit to the initial decay produces a daily turnover of approximately $((435,000-60,000)/\mu l)6$ d or $62,500/d$. According to the method of the invention, the turnover rate represents the combination of clearance of senescent platelets and consumption in the repair of vascular lesions, in accordance with the stochastic model of vascular injury disclosed herein, namely:

$$T_t = T_0 + (\pi - \sigma - \lambda\mu)t$$

and, for $\pi=0$:

$$T_t = T_0 - (\sigma + \lambda\mu)t$$

With $\sigma=0.1{*}T_0$, or $43,500/\mu l$ per day, this yields an estimate for consumption in vascular injury repair of $\lambda\mu=19,000/0$. In general, $\sigma$ can be time-dependent.

Example 2

Concurrently determine $\sigma$, $\lambda\mu$ and from survival curves recorded with labeled platelets for normal subjects and patients with stable thrombocytopenia (see Table 1 showing data extracted from FIG. 1 of HansonSlichter1985).

Survival curves recorded with $^{51}$Cr-labeled platelets for normal subjects and for patients with thrombocytopenia secondary to bone marrow hypoplasia display a linear or near-linear decay in the normalized count, $v(t)=N(t)/N(t=0)$, of the number, $N(t)$, of labeled platelets remaining at time t after (re-)transfusion of autologous platelets. In these subjects, platelets are produced at a rate, $\pi$, matching the rate of loss due to senescence, $\sigma$, and vascular injury repair, $\lambda\mu$, and in this steady state, the method of the invention, as disclosed in form of pseudocode, permits the determination of $\lambda$, and $\mu$ for fixed $\sigma=0.1$. Alternatively, the simulation of the stochastic process by the algorithm disclosed herein as pseudocode permits the estimation of $\lambda\mu$ as follows:

|  | $\Lambda\mu$ |
|---|---|
| Cohort 1 (normal subjects, 250,000, first set in Table 1): | 1,300/µl |
| Cohort 2 (thrombocytopenic, 62,000/ul, second set in Table 1): | 3,300/µl |
| Cohort 3 (thrombocytopenic, 37,000/ul, third set in Table 1): | 5,300/µl |
| Cohort 4 (thrombocytopenic, 19,000/ul, fourth set in Table 1): | 9,700/µl |

Example 3

Determine $\lambda\mu$ from the distribution of transfusion intervals for individual patients receiving chemotherapy for the treatment of hematologic malignancies (FIG. 2, Table 2). From the transfusion history, comprising a record of multiple platelet transfusions, or a selected portion thereof, limited to a preset range of dates or times, generate a histogram of the interval, $\tau$, between successive transfusions (aka "transfusion interval"): $\tau$ represents the nominal time for the platelet count to decay from the maximum attained following the infusion of platelets, corrected for splenic sequestration (Aster1966), to a predetermined minimal value of, e.g., 10,000/ul (aka "transfusion threshold" or "transfusion trigger"). Given the volume transfused, at the transfusion threshold, the rate $\lambda\mu$ may be estimated from the distribution of $\tau$ by performing the following steps:

Step 1—Determine the expected maximum total platelet count following transfusion of a known volume of platelets;
  NOTE—200 ml of a pooled platelet suspension, comprising 4 units of $0.5*10^{11}$ platelets each, contains $4*10^{11}$ platelets; transfusion, at a "trigger" level of 10,000/µl, to an individual with a typical blood volume of 5,000 ml, produces an expected maximum count increment of ~40,000/µl, rapidly reduced to ~26,000/µl by splenic sequestration of ~35% of the newly transfused platelets (Aster1966, Harker1969), thus a maximum expected post-transfusion count of 36,000/µl (=10,000/ul+26,000/ul) in circulation, corresponding to a total platelet count of 55,380/µl (=(36,000/0.65)/µl)

Step 2—Tally total count reflecting the loss of senescent platelets, at a daily rate of 10% of 55,380/µl, as well as the consumption of platelets in maintaining vascular integrity, at the unknown rate, $\lambda$;

Step 3—Determine $\lambda$ so as to ensure the reduction of the circulating count back to the trigger level in a preset elapsed time, $\tau$;

With reference to FIG. 2, this method yields the following estimates: with 200 ml of transfused platelets, a daily rate of $\lambda=17,200$/µl returns the count to the trigger level of 10,000 µl in $\tau=2$ d, a rate of $\lambda=10,300$/µl does so in 3 d; with a volume of 250 ml of transfused platelets, a daily rate of $\lambda=13,200$/µl lowers the count to the trigger level in 3 d.

This method thus permits the determination of $\lambda$ from the analysis of the patient's transfusion history comprising a record of dates and times of platelet transfusions.

Example 4

Optimize dosing: INCREASE the number of platelets transfused in order to DECREASE the frequency and cost of transfusion support.

As illustrated here for a linear decay in platelet count, for patients with minimal or no platelet production, a higher average level may be maintained, while reducing total expense, by increasing the volume of each transfusion, thereby increasing the time between transfusions.

A platelet transfusion comprising 3E11 platelets (e.g. in the form of a platelet pool of 6 units of 0.5E11 platelets each), given at a level of 10,000/µl, is expected to produce a maximum post-transfusion count of 70,000/µl (assuming a total blood volume of 5 liters) and 46,200/µl after splenic sequestration. Assuming removal of senescent platelets, at a rate of 10% of the initial value, and assuming a daily rate of platelet consumption for maintaining vascular integrity of $kV=12,000$/µl, the average transfusion interval, dt, would be 1.8 days, yielding an expected number of 60/dt transfusions over a 60 day period. Assuming $500 per platelet product, and $1,000 for the total cost of administering the platelets (Shander2010), the total expected cost would be ~$49.2K.

Administering two bags of platelets, at a total cost of 2*$500+$1,000, increases the average dt to 2.92 days, and reduces the expected number of transfusions accordingly, thereby lowering the expected total cost to $41.1K.

Example 5

Continuous administration of platelets at a rate maintaining a preset platelet level.

To maintain the platelet count at a preset level, administer platelets continuously—for example by platelet drip—and set the rate of infusion so as to match the rate of loss determined by the methods disclosed herein, to establish a de-facto steady state (or near-steady state, with excursions of the platelet count maintained in a preset band), by adjusting the rate of infusion to match the rate of platelet loss due to clearance of senescent platelets and consumption of platelets in maintaining vascular integrity (and possible additional factors, notably the antibody-mediated accelerated clearance of opsonized platelets).

Thus:
  determine the rate of platelet loss by analyzing survival curve(s) following platelet infusion for a patient receiving chemotherapy, with (at best) a low rate of platelet production;
  by the methods of the invention, determine the rate of consumption of platelets in maintaining vascular integrity;
  set a target platelet count no lower than the level corresponding to the total number of platelets lost per day, computed from the said rate of platelet loss;
  administer platelets by continual infusion at a rate exceeding the said rate of loss by a preset margin;
  after a preset time, reduce the said rate of administration to the said rate of loss in order to maintain the platelet count at a preset level The specific methods and processes described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The stochastic process of the invention, preferably in its analytical formulation, provides the basis for the design of specific platelet administration regimens, as exemplified herein below, namely by permitting, in analogy to pharmacokinetic and pharmacodynamic ("PK/PD") modeling of modern pharmacotherapy, where "pharmacokinetics describes the drug concentration-time courses in body fluids resulting from administration of a certain drug dose" and "pharmacodynamics the observed effect resulting from a certain drug concentration" (Meibohm1997, Int J Clin Pharmacoll Ther 1997, 35(10):401-13).

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

All References, Patents and Applications Mentioned Herein are Hereby Incorporated by Reference Assigner2014—Assigner A, Platelets and infection—an emerging role of platelets in viral infection. Frontiers in Immunology 2014; 5, Article 649, 1-12.

Aster1966—Aster R H. Pooling of Platelets in the Spleen: Role in the Pathogenesis of "Hypersplenic" Thrombocytopenia. J Clin Investigation 1966; 45(5): 645-57.

Dowling2010—Dowling M R, Josefsson E C, Henley K J, Hodgkin P D, Kile B T. Platelet senescence is regulated by an internal timer, not damage inflicted by hits. Blood 2010; 116(10): 1776-78

Estcourt2012—Estcourt L, Stanworth S, Doree C, Hopewell S, Murphy M F, Tinmouth A et al. Prophylactic platelet transfusion for prevention of bleeding in patietns with haematological disorders after chemotherapy and stem cell transplantation. Cochrane Database Syst Rev 2012; May 16; 5: CD004269

Goerge2008—Goerge T, Ho-Tin-Noe B, Carbo C, Benarata C, Remold-O'Donnell E, Zhao B-Q et al Inflammation induces hemorrhage in thrombocytopenia. Blood 2008; 111(10): 4958-64

Hanson1985—Hanson S R, Slichter S J, Platelet Kinetics in Patients with Bone Marrow Hypoplasia: Evidence for a Fixed Platelet Requirement, Blood 1985; 66:1105-09

Harker1969—Harker L A, Finch C A. Thrombokinetics in Man. J Clin Investigation 1969; 48:963-74

Hillyer2007—Hillyer C D. Blood Banking and Transfusion Medicine: Basic Principles & Practice. Churchilll, Livingston, Elsevier, $2^{nd}$ Ed, 2007. Chapt 33, p 458

Ho-Tin-Noe, B, Demers M, Wagner D D. How platelets safeguard vascular integrity. J Thromb Haemost 2011; 9(Suppl 1): 56-65.

Nachman2008—Nachman R L, Rafii S. Platelets, Petechiae, and Preservation of the Vascular Wall. N Engl J Med 2008; 359(12): 1261-70.

Psaila2011—Psaila B, Bussel J B, Frelinger A L, Babula B, Linden M D, Li, Y, et al. Differences in Platelet Function In Patients with Acute Myeloid Leukaemia and Myelodysplasia Compared to Equally Thrombocytopenic Patients with Immune Thrombocytopenia. J Thromb Haemost. 2011; 9(11): 2302-10.

Slichter2005—Slichter S J, Davis K, Enright H, Braine H, Gernsheimer T, Kao K J, et al. Factors affecting post-transfusion platelet increments, platelet refractoriness, and platelet transfusion intervals in thrombocytopenic patients. Blood. 2005; 105:4106-14

Shander2010—Shander A, Hofmann A, Ozawa S, Theusinger O M, Gombotz H, Spahn D R. Activity-based costs of blood transfusion in surgical patients at four hospitals. Transfusion 2010; 50: 753-65.

Strobel2008—Strobel E. Hemolytic Transfusion Reactions. Transfus Med Hemother 2008; 35:346-353

TRAP1997—TRAP Study Group. Leukocyte reduction and ultraviolet B irradiation of platelets to prevent alloimmunization and refractoriness to platelet transfusions. The Trial to Reduce Alloimmunization to Platelets Study Group. New Engl J Med 1997; 337(26):1861-69.

What is claimed is:

1. A method for personalizing a platelet administration regimen for a patient with reduced platelet production, comprising:

recording a platelet survival curve by determining concentration of platelets at a plurality of times following platelet transfusion;

analyzing the platelet survival curve to determine value(s) proportionally representing both the extent and frequency of vascular injury, expressed in terms of platelet quantities or platelet concentration required to repair said vascular injury;

using said value(s) to determine a platelet transfusion requirement for maintaining vascular integrity; and administering not substantially less than the amount of platelets to satisfy said platelet transfusion requirement, to the patient.

2. The method of claim 1 wherein the times for determining platelet concentration span a 1-24 hour period.

3. The method of claim 1 wherein the concentration determined is of labeled or unlabeled platelets.

4. The method of claim 1 further including using said value(s) to determine a platelet transfusion prescription including the platelet quantity required for each of a plurality of transfusions performed at a plurality of times.

5. The method of claim 4 wherein the platelets are continuously transfused into the patient.

6. The method of claim 4 wherein the interval between transfusions and the quantity of platelets administered at each transfusion is re-determined so as to increase said interval.

7. A tracking method for preserving inventory of platelets having a particular antigen type or antigen profile, comprising:
  determining virtual or actual inventory quantity of platelets having a particular antigen type or profile;
  determining quantity of platelets having a particular antigen type or profile to be given a particular patient, by:
  recording a platelet survival curve for said patient by determining concentration of platelets at a plurality of times following platelet transfusion;
  analyzing the platelet survival curve to determine value(s) proportionally representing both the extent and frequency of vascular injury, expressed in terms of platelet quantities or platelet concentration required to repair said vascular injury;
  using said value(s) to determine a platelet transfusion requirement for maintaining vascular integrity; and
  removing said platelet transfusion requirement from inventory.

8. The method of claim 7 further including replenishing said platelet transfusion requirement into inventory.

9. The method of claim 7 further including removing from inventory platelets which reach or have passed an expiration period.

10. The method of claim 9 further including replenishing said expired platelets into inventory.

11. The method of claim 7 further including administering not substantially more than the amount of platelets to satisfy said platelet transfusion requirement to the patient in accordance with said patient's molecular attribute profile and antibody status.

12. The method of claim 7 wherein removing platelets from inventory means not exclusively reserving the right to use them as against any other party holding or having rights to said removed platelets.

13. The method of claim 7 wherein replenishing platelets into inventory means exclusively reserving the right to use them as against any other party holding or having rights to said replenished platelets.

14. The method of claim 7 wherein the times for determining platelet concentration span a 24-48 hour period.

15. The method of claim 7 wherein the concentration determined is of labeled or unlabeled platelets.

16. The method of claim 7 further including using said value(s) to determine a platelet transfusion prescription including the platelet quantity required for each of a plurality of transfusions performed at a plurality of times.

17. A method for personalizing a platelet administration regimen for a patient with reduced platelet production, comprising:
  recording a platelet survival curve by determining concentration of platelets at a plurality of times following platelet transfusion;
  analyzing the platelet survival curve to determine value(s) proportionally representing both the extent and frequency of vascular injury, expressed in terms of platelet quantities or platelet concentration required to repair said vascular injury;
  using said value(s) to determine a platelet transfusion requirement for maintaining vascular integrity; and
  administering not substantially more than the amount of platelets to satisfy said platelet transfusion requirement, to the patient.

18. The method of claim 17 wherein the times for determining platelet concentration span a 1-24 hour period.

19. The method of claim 17 further including using said value(s) to determine a platelet transfusion prescription including the platelet quantity required for each of a plurality of transfusions performed at a plurality of times.

20. The method of claim 17 wherein the interval between transfusions and the quantity of platelets administered at each transfusion is re-determined so as to increase said interval.

* * * * *